(12) United States Patent
Gorr et al.

(10) Patent No.: US 12,037,374 B2
(45) Date of Patent: Jul. 16, 2024

(54) PEPTIDES, HYDROGEL COMPOSITIONS AND METHODS OF USE THEREOF

(71) Applicant: Regents of the University of Minnesota, Minneapolis, MN (US)

(72) Inventors: Sven-Ulrik Gorr, Minneapolis, MN (US); Conrado Aparicio, Minneapolis, MN (US); Zhou Ye, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 17/098,629

(22) Filed: Nov. 16, 2020

(65) Prior Publication Data

US 2021/0147496 A1 May 20, 2021

Related U.S. Application Data

(60) Provisional application No. 62/936,118, filed on Nov. 15, 2019.

(51) Int. Cl.
*C07K 14/47* (2006.01)
*A61K 47/10* (2017.01)

(52) U.S. Cl.
CPC .............. *C07K 14/47* (2013.01); *A61K 47/10* (2013.01)

(58) Field of Classification Search
None
See application file for complete search history.

(56) References Cited

U.S. PATENT DOCUMENTS 8,569,449 B2 10/2013 Gorr
9,914,750 B2 3/2018 Gorr

OTHER PUBLICATIONS

Ye et al. (Nanoscale. Dec. 20, 2018; 11(1): 266-275) (Year: 2018).*
Hu et al. (Chem. Soc. Rev., 2018, 47, 6917) (Year: 2018).*
Ng et al. (Advanced Drug Delivery Reviews 78 (2014) 46-62) (Year: 2014).*
Hirt et al. (Antimicrob Agents Chemother. Oct. 2013;57(10):4903-10) (Year: 2013).*
Do et al. (J. Phys. Chem. B 2013, 117, 10759-10768) (Year: 2013).*
Willoughby et al. (Surv. Ophthalmol. 47 (2) Mar.-Apr. 2002) (Year: 2002).*
Gorr, S , et al., "In vivo activity and low toxicity of the secondgeneration antimicrobial peptide DGL13K", PLoS One 14(5), e0216669, 14 pages (2019).
Gorr, S , et al., "The antimicrobial peptide DGL13K is active against resistant gram-negative bacteria and subinhibitory concentrations stimulate bacterial growth without causing resistance", https://doi.org/10.1101/020.05.08.085282 , 27 pages (2020).
Hirt, H , et al., "A D-enantiomer of the antimicrobial peptide GL13K evades antimicrobial resistance in the Gram positive bacteria *Enterococcus faecalis* and *Streptococcus gordonii*", PLoS One 13(3), e0194900, 16 pages (2018).
Hirt, H , et al., "Antimicrobial Peptide GL13K Is Effective in Reducing Biofilms of Pseudomonas aeruginosa", Antimicrobial Agents and Chemotherapy 57(10), 4903-4910 (2013).
Ye, Z , et al., "Self-assembly dynamics and antimicrobial activity of all L- and D-amino acid enantiomers of a designer peptide", Nanoscale 11, 266-275 (2019).
Kim, G , et al., "Fabrication and Characterization of Hydrophobic Cellulose Nanofibrils/SilicaNanocompositeswith-Hexadecyltrimethoxysilane", Polymers 14 (833), 17 pages (2022).
Rana, T , et al., "Hydrogels: A Novel Drug Delivery System", J Biomed Res Environ Sci. 1(8), 439-451 (2020).
Wang, G, et al., "The evolution of the antimicrobial peptide database over 18 years: Milestones and new features", Protein Science 31, 92-106 (2022).

\* cited by examiner

*Primary Examiner* — Sergio Coffa
(74) *Attorney, Agent, or Firm* — Viksnins Harris Padys Malen LLP

(57) ABSTRACT

The invention provides antibiotic BPI Fold Containing Family A Member 2 (BPIFA2) peptides, compositions comprising a BPIFA2 peptide, hydrogels comprising a BPIFA2 peptide, nanofibrillar networks comprising a BPIFA2 peptide, and tissue scaffolds comprising BPIFA2 peptides. The peptide, compositions, hydrogels nanofibrillar networks and tissue scaffolds are useful for medical therapy in an animal.

12 Claims, 12 Drawing Sheets
(10 of 12 Drawing Sheet(s) Filed in Color)
Specification includes a Sequence Listing.

Figure 11
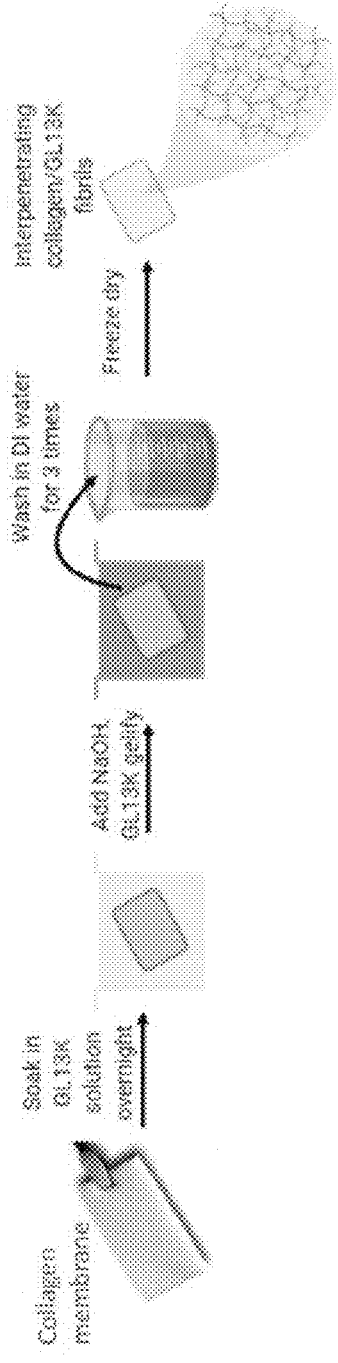
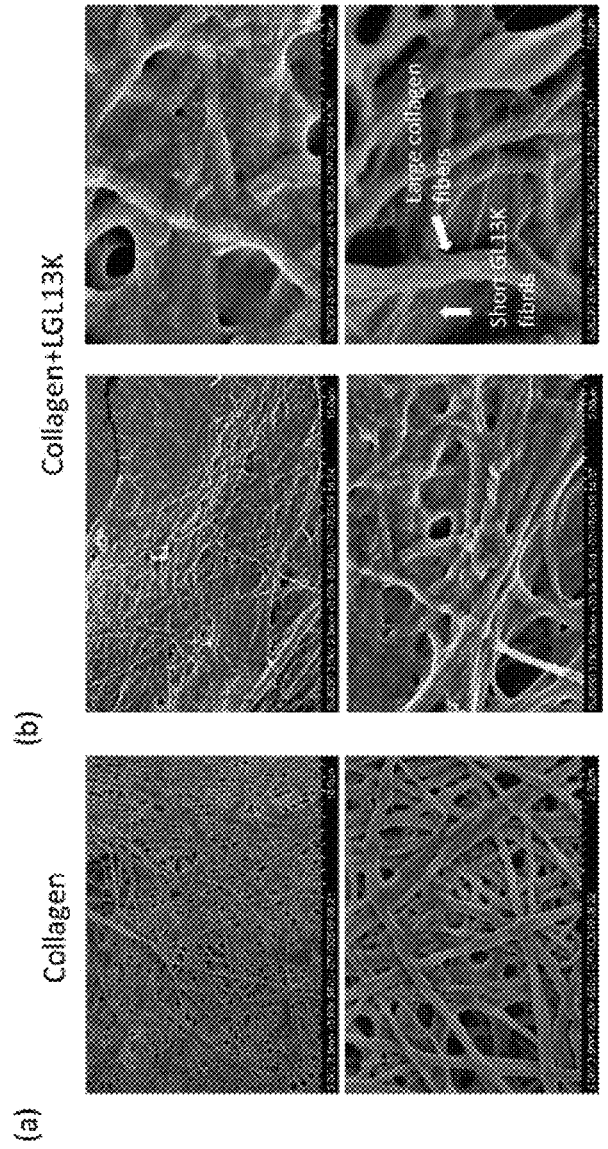
Figures 12A and 12B

PEPTIDES, HYDROGEL COMPOSITIONS AND METHODS OF USE THEREOF

RELATED APPLICATION

This application claims priority to U.S. Provisional Application No. 62/936,118 that was filed on Nov. 15, 2019. The entire content of the application referenced above is herein incorporated by reference in its entirety.

SEQUENCE LISTING

The instant application contains a Sequence Listing which has been submitted electronically in ASCII format and is hereby incorporated by reference in its entirety. Said ASCII copy, created on Jan. 19, 2021, is named 09531_498US1_SL.txt and is 5,328 bytes in size.

BACKGROUND OF THE INVENTION

Currently there is a need for additional agents that are useful for treating wounds, including cuts and lacerations, and penetrations into deeper tissues such as after surgical interventions. In particular, there is a need for peptide, hydrogels, nanofibrillar networks, and tissue scaffolds with improved properties, such as, for example, improved activity, potency, patient acceptance and/or reduced toxicity and low propensity to cause bacterial resistance.

SUMMARY OF THE INVENTION

In one aspect the present invention provides a composition comprising an isolated and purified BPI Fold Containing Family A Member 2 (BPIFA2) peptide of 15 to 50 amino acids in length comprising the amino acid sequence of SEQ ID NO: 1 or SEQ ID NO: 2 operably linked to a polypeptide linker of 2-37 amino acids in length In one aspect the present invention provides an isolated and purified BPI Fold Containing Family A Member 2 (BPIFA2) peptide of 21 to 50 amino acids in length comprising the amino acid sequence of SEQ ID NO: 12 or SEQ ID NO: 13.

In one aspect the present invention provides a composition comprising an isolated and purified BPI Fold Containing Family A Member 2 (BPIFA2) peptide operably linked to a polyethylene glycol (PEG), wherein the peptide is SEQ ID NO: 1, SEQ ID NO: 2, SEQ ID NO: 3, SEQ ID NO: 10, SEQ ID NO: 11, SEQ ID NO: 12 or SEQ ID NO: 13.

In one aspect the present invention provides a hydrogel comprising a BPI Fold Containing Family A Member 2 (BPIFA2) peptide of 13 to 50 amino acids in length comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 10, SEQ ID NO: 11, SEQ ID NO: 12, or SEQ ID NO: 13.

In one aspect the present invention provides a composition comprising the hydrogel described herein and a second agent.

In one aspect the present invention provides a nanofibrillar network comprising the hydrogel described herein, and a polymer.

In one aspect the present invention provides a tissue scaffold comprising the nanofibrillar network described herein.

In one aspect the present invention provides a method of regenerating tissue in an animal comprising contacting the tissue scaffold described herein to the animal. In certain embodiments, the animal is a human.

In one aspect the present invention provides a method for preventing or treating a wound infection in an animal comprising administering (a) the composition described herein, (b) the hydrogel described herein, (c) the nanofibrillar network described herein, or (d) the tissue scaffold described herein to the animal.

In one aspect the present invention provides a peptide described herein, a composition described herein, a hydrogel described herein, a nanofibrillar network described herein, or a tissue scaffold described herein for use in medical therapy.

In one aspect the present invention provides a peptide described herein, a composition described herein, a hydrogel described herein, a nanofibrillar network described herein, or a tissue scaffold described herein for use in medical therapy to prevent or treat an infection.

In one aspect the present invention provides a peptide described herein, a composition described herein, a hydrogel described herein, a nanofibrillar network described herein, or a tissue scaffold described herein for use in treating a wound.

In one aspect the present invention provides a use of a peptide described herein, a composition described herein, a hydrogel described herein, a nanofibrillar network described herein, or a tissue scaffold described herein to prepare a medicament for prophylactically and/or therapeutically treating a wound infection in an animal.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 11: Schematics of fabricating collagen+GL13K membrane.

FIGS. 12A and 12B: SEM images of (a) the collagen membrane and (b) the collagen+LGL13K interpenetrated nanofibrillar network.

DETAILED DESCRIPTION OF THE INVENTION

Figure 1:
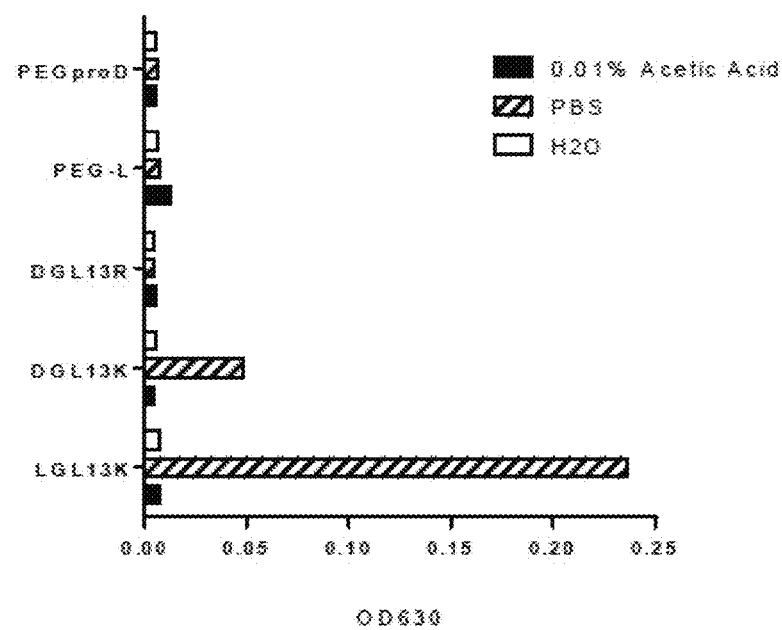
FIG. 1: Turbidity of peptide solutions at 630 nm. Peptides were suspended in 0.01% acetic acid (our standard peptide solvent), Phosphate-Buffered Saline (PBS), pH 7.4 or dH2O.

The innate immune system produces a variety of antimicrobial proteins that serve as a first line of defense against bacterial, viral and fungal infections. Human host-defense proteins include lysozyme, lactoferrin, secretory leukoprotease inhibitor, beta defensins, alpha defensins (human neutrophil peptides), histatins, calgranulin A and B and the human cathelicidin hCAP18 (LL37). Many of these proteins are cationic and it has been found that depletion of cationic proteins from airway fluid eliminates its antibacterial activity. In addition to these established antimicrobial proteins, a new gene family of potential antimicrobial proteins was identified on human chromosome 20q11. The corresponding proteins are related to several previously known animal proteins, including mouse PLUNC (BPIFA1), bovine BSP30 (BPIFA2), and rodent PSP (BPIFA2). Several investigators have noted that the PLUNC family proteins (now renamed BPI Fold Containing Family—BPIF) appear to be structurally related to the antibacterial and anti-inflammatory protein Bactericidal Permeability-Increasing protein (BPI) and LPS-binding protein (LBP). The inventors tested the hypothesis that peptides based on the BPIFA2 sequence are antibacterial to the opportunistic pathogens P. aeruginosa and A. actinomycetemcomitans, which infect the airways and oral cavity.

A "biofilm" is a complex organization of bacteria that are anchored to a surface via a bacterially extruded exopolysaccharide matrix and grow into differentiated towers that can be several hundred bacteria in height. The extruded exopolysaccharide matrix, which comprises more than 90% of the biofilm, envelopes the bacteria and provides protection from phagocytosis and oxidative burst mechanisms, both in natural environments and in the host.

Bacteria within biofilms are also resistant to the host's humoral defense systems because of a lack of accessibility by immunoglobulin and complement. The attachment of bacteria to a surface triggers the expression of a cassette of genes, which results in the formation of a biofilm. A "biofilm phenotype" confers to a bacterium a reduced metabolic activity and enhanced antibiotic resistance in comparison with the corresponding planktonic phenotype.

A 'biofilm-producing bacterium" or "biofilm bacterium" is a bacterium capable of producing, forming, and/or accumulating a biofilm in vitro or in vivo, e.g., on artificial and cellular surfaces. Biofilm bacteria have been demonstrated to be highly resistant to growth in standard planktonic (i.e., free-floating) culture, attributed to differences in gene expression.

BPI Fold Containing Family A Member 2 (BPIFA2) Peptides

BPIFA2 (former name: Parotid Secretory Protein (PSP)) expression is regulated by bacteria and the cytokine TNFα. BPIFA2 binds lipopolysaccharide (LPS). LPS binding does not depend on glycosylation. It was observed that BPIFA2 peptides inhibit biofilm formation but do not eliminate established biofilm.

The present inventors have designed several peptides based on the sequences of human BPIFA2. The peptide GL13NH2 has been developed into a family of peptides with different biological and chemical properties (Table 1). The peptide sequences of GL13K and GL13R are altered at 2-4 of the 13 amino acids compared to the previous patents (U.S. Pat. Nos. 8,569,449 and 9,914,750). Pro-peptide and PEG extensions were not claimed previously.

TABLE 1

| Name, charge and sequence of peptides discussed herein | | | |
|---|---|---|---|
| Name | Charge @ pH 7 | Sequence | SEQ ID NO |
| LGL13K | 5 | NH$_2$—Gly—Lys—Ile—Ile—Lys—Leu—Lys—Ala—Ser—Leu—Lys—Leu—Leu—CONH$_2$ | 1 |
| DGL13K | 5 | NH$_2$—Gly—d-Lys—d-Ile—d-Ile—d-Lys—d-Leu—d-Lys—d-Ala—d-Ser—d-Leu—d-Lys—d-Leu—d-Leu—CONH$_2$ | 2 |
| DGL13R | 5 | NH$_2$—Gly—d-Arg—d-Ile—d-Ile—d-Arg—d-Leu—d-Arg—d-Ala—d-Ser—d-Leu—d-Arg—d-Leu—d-Leu—CONH$_2$ | 3 |

TABLE 1-continued

Name, charge and sequence of peptides discussed herein

| Name | Charge @ pH 7 | Sequence | SEQ ID NO |
|---|---|---|---|
| PEG-LGL13K | 5 | PEG—Gly—Lys—Ile—Ile—Lys—Leu—Lys—Ala—Ser—Leu—Lys—Leu—Leu—CONH$_2$ | 4 |
| PEG-DGL13K | 5 | PEG—Gly—d-Lys—d-Ile—d-Ile—d-Lys—d-Leu—d-Lys—d-Ala—d-Ser—d-Leu—d-Lys—d-Leu—d-Leu—CONH$_2$ | 5 |
| PEG-pro-DGL13K | 5 | PEG—d-Leu—Gly—Gly—d-Ala—Gly—d-Lys—d-Ile—d-Ile—d-Lys—d-Leu—d-Lys—d-Ala—d-Ser—d-Leu—d-Lys—d-Leu—d-Leu—CONH$_2$ | 6 |
| PEG-E4-pro-DGL13K | 1 | PEG—d-Glu—d-Glu—d-Glu—d-Glu—d-Leu—Gly—Gly—d-Ala—Gly—d-Lys—d-Ile—d-Ile—d-Lys—d-Leu—d-Lys—d-Ala—d-Ser—d-Leu—d-Lys—d-Leu—d-Leu—CONH$_2$ | 7 |
| Pro = pro-peptide | | d-Leu—Gly—Gly—Ala | 8 |
| E4 = acidic residues to neutralize peptide charge | | d-Glu—d-Glu—d-Glu—d-Glu | 9 |
| pro-LGL13K | | NH$_2$—d-Leu—Gly—Gly—d-Ala—Gly—Lys—Ile—Ile—Lys—Leu—Lys—Ala—Ser—Leu—Lys—Leu—Leu—CONH$_2$ | 10 |
| pro-DGL13K | | NH$_2$—d-Leu—Gly—Gly—d-Ala—Gly—d-Lys—d-Ile—d-Ile—d-Lys—d-Leu—d-Lys—d-Ala—d-Ser—d-Leu—d-Lys—d-Leu—d-Leu—CONH$_2$ | 11 |
| E4-pro-LGL13K | | NH$_2$—d-Glu—d-Glu—d-Glu—d-Glu—d-Leu—Gly—Gly—d-Ala—Gly—Lys—Ile—Ile—Lys—Leu—Lys—Ala—Ser—Leu—Lys—Leu—Leu—CONH$_2$ | 12 |
| E4-pro-DGL13K | | NH$_2$—d-Glu—d-Glu—d-Glu—d-Glu—d-Leu—Gly—Gly—d-Ala—Gly—d-Lys—d-Ile—d-Ile—d-Lys—d-Leu—d-Lys—d-Ala—d-Ser—d-Leu—d-Lys—d-Leu—d-Leu—CONH$_2$ | 13 |

PEG (polyethylene glycol) = H$_2$N—CH$_2$—CH$_2$—O—CH$_2$—CH$_2$—C(=O)—(Peptide)

GL13 = base peptide.
Prefix L or D for amino acid enantiomers.
Suffix K or R, indicates amino acid substitutions of four charged residues in the GL13NH$_2$ peptide.
Pro = pro-peptide (SEQ ID NO: 8), a putative proteolytic cleavage site.
E4 = acidic residues to neutralize peptide charge (SEQ ID NO: 9).

In one aspect the present invention provides a composition comprising an isolated and purified modified BPIFA2 peptide of 13 to 50 amino acids in length comprising the amino acid sequence of SEQ ID NO: 1 or SEQ ID NO: 2 operably linked to a polypeptide linker of 2-37 amino acids in length. In certain embodiments, the peptide is 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In certain embodiments, the peptide is between 15 and 25 amino acids in length. In certain embodiments, the peptide is linked at its C-terminus to the linker. In certain embodiments, the peptide is linked at its N-terminus to the linker. In certain embodiments, a peptide is linked at both its N-terminus and C-terminus to a linker. In certain embodiments, the linker is 2-37 amino acids long. In certain embodiments, the linker is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 amino acids in length. In certain embodiments, the linker comprises a proteolytic cleavage site. In certain embodiments, the proteolytic cleavage site is a target for bacterial or animal proteases. In certain embodiments, the linker sequence is LGGA (SEQ ID NO: 14). In certain embodiments, the peptide consists of SEQ ID NO: 10 or SEQ ID NO: 11. In certain embodiments the composition comprising the peptide and linker is 17-87 amino acids in length. In certain embodiments, the composition is 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 74, 76, 77, 78, 79, 80, 81, 82, 83, 84, 85, 86, or 87 amino acids in length.

In one aspect the present invention provides an isolated and purified modified BPIFA2 peptide of 21 to 50 amino acids in length comprising the amino acid sequence of SEQ ID NO: 12 or SEQ ID NO: 13. In certain embodiments, the peptide is 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In certain embodiments, the peptide is between 21 and 30 amino acids in length. In certain embodiments, the peptide consists of SEQ ID NO: 12 or SEQ ID NO: 13. In certain embodiments, the BPIFA2 peptide is operably linked to a therapeutic agent.

In one aspect the present invention provides a composition comprising an isolated and purified modified BPIFA2 peptide operably linked to a polyethylene glycol (PEG), wherein the peptide is SEQ ID NO: 1, SEQ ID NO: 2, SEQ ID NO: 3, SEQ ID NO: 10, SEQ ID NO: 11, SEQ ID NO: 12 or SEQ ID NO: 13. In certain embodiments, the PEG is operably linked to the BPIFA2 peptide at its N-terminal end. In certain embodiments, the BPIFA2 peptide inhibits LPS-activity. In certain embodiments, the BPIFA2 peptide is operably linked to a therapeutic agent.

Peptide Hydrogels

It has been demonstrated herein that the antimicrobial peptide GL13K can form a hydrogel when the peptide is reacted with dilute sodium hydroxide. In certain embodiments, the charged residues that allow gelation of the antimicrobial peptides are Lysines but not Arginines. In certain embodiments, the antimicrobial peptide is comprised of D-amino acids. In certain embodiments, the antimicrobial peptide may carry N-terminal polyethyleneglycol unit of MW=116. In certain embodiments, the antimicrobial peptide can be extended at the N-terminus by a peptide-linker. In certain embodiments, the peptide-linker can be a proteolytic cleavage site to create a potential prodrug. In certain embodiments, the pro-sequence is LGGA (SEQ ID NO: 14).

The hydrogels of the present invention are less toxic in vitro and in vivo than the unmodified peptide. It was determined that PEGylated GL13K is less toxic than unmodified peptide. In certain embodiments, the hydrogel formation is prepared using a sodium hydroxide concentration of 6.6-16.7 mM. Hydrogel formation occurs at peptide concentrations above 0.8 mg/ml.

In one aspect the present invention provides a hydrogel comprising a peptide of 13 to 50 amino acids in length comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 10, SEQ ID NO: 11, SEQ ID NO: 12, or SEQ ID NO: 13. In certain embodiments, the peptide is operably linked to a polyethylene glycol (PEG). In certain embodiments, the PEG is operably linked to the BPIFA2 peptide at its N-terminal end. In certain embodiments, the BPIFA2 peptide inhibits LPS-activity. In certain embodiments, the hydrogel is less toxic than the peptide in its soluble form. In certain embodiments, the peptide is operably linked to a therapeutic agent.

In one aspect the present invention provides a composition comprising the hydrogel described herein and a second agent. In certain embodiments, the second agent is a small molecule or biomolecule. In certain embodiments, the small molecule is a steroid hormone or an antibiotic. In certain embodiments, the biomolecule is a peptide or carbohydrate. In certain embodiments, the second agent is a solid support. In certain embodiments, the solid support is a medical device. In certain embodiments, the medical device is a soft contact lens, a dental implant, an orthopedic implant, or a membrane for guided tissue regeneration.

In one aspect the present invention provides a nanofibrillar network comprising the hydrogel as described herein and a polymer. In certain embodiments, the BPIFA2 peptide can be gelled as a nanofibrillar network interpenetrated with a fibrillar network of polymers to form hydrogels or membranes. In certain embodiments, the polymer is a natural or synthetic polymers, including collagen, gelatin, silk fibroin, fibrin, elastin, elastin-like polymer, chitosan, starch, alginate, chondroitin sulphate, dextran, agar, carrageenans, gellan gum, cellulose, polycaprolactone, poly(l-lactic acid), poly(lactide-co-glycolide). In certain embodiments, the polymer is collagen. In certain embodiments, the nanofibrillar network is not cytotoxic to human cells. In certain embodiments, the nanofibrillar network has increased antimicrobial properties as compared to a collagen membrane.

BPIFA2 peptides form interpenetrated short nanofibrils and do not destroy the original nanostructure of the other hydrogel/membrane. In certain embodiments, the range of peptide concentration and sodium hydroxide concentration used is the same as for the peptide gel alone. Interpenetrated peptide nanofibrils with collagen fibrils (e.g., collagen+GL13K) change the membrane to be much more hydrophobic than collagen fibrils alone. The high hydrophobicity of collagen+GL13K membrane reduces its biodegradability from water-borne agents, such as collagenase, compared to collagen membranes. The collagen+GL13K membrane is antimicrobial as it reduces the number of live *Streptococcus gordonii* bacteria on the surface of the membrane compared to the collagen membrane. The interpenetrated collagen+GL13K membrane is not cytotoxic to human gingival fibroblast.

In one aspect the present invention provides a tissue scaffold comprising the nanofibrillar network described herein. Collagen membranes (ACE Surgical Supply CO., Inc., Brockton, Mass.) were punched to make disks of 6 mm in diameter. LGL13K was dissolved in deionized (DI) water at a concentration of 14 mg/ml. The collagen disc was submerged in 100 µl LGL13K solution in the well of a 96-well plate at 4° C. overnight. Then 25 µl of 0.1 N NaOH solution was added to the well to gelify the LGL13K solution at 4° C. overnight. The LGL13K-incubated collagen disc was washed in DI water for three times and freeze-dried overnight to get the collagen+LGL13K membrane.

In summary, the present inventors have prepared a PEGylated version of DGL13K, which retains antibacterial activity with no increase in toxicity. PEG-DGL13K is soluble in PBS while DGL13K is only soluble in dilute acetic acid. Thus, PEG-extended peptides were useful for hydrogel formation.

LGL13K is random coil in solution but rearranges to form β-turns/sheets in the presence of biological membranes, i.e., in the active form. Thus, GL13K peptides form the conformation compatible with hydrogel formation.

Figure 2:
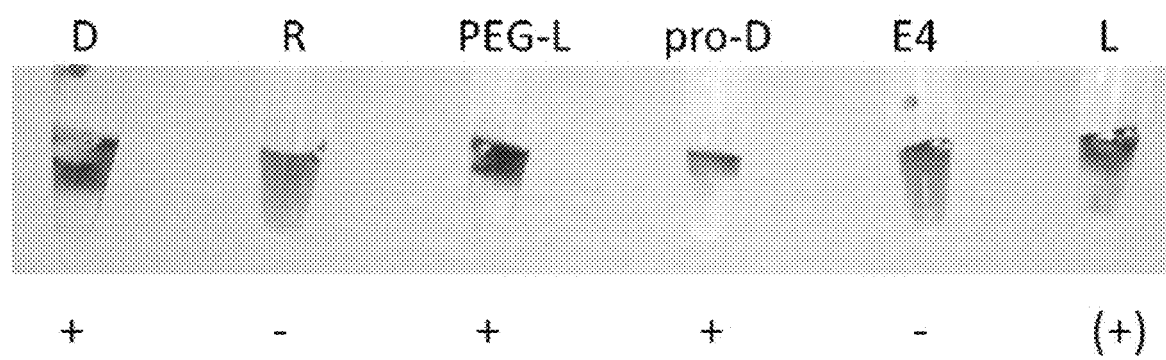
FIG. 2: Hydrogel formation of GL13 peptides. Hydrogels are overlaid with Crystal Violet solution. D=DGL13K; R=DGL13R; PEG-L=PEG-LGL13K; pro-D=PEG-pro-DGL13K; E4=PEG-E4-pro-DGL13K; L=LGL13K.

The peptides LGL13K and DGL13K are cationic (Charge +5), amphipathic peptides with antibacterial activity against Gram negative and Gram positive bacteria, their biofilms and drug-resistant strains. We have determined that the hydrophobic amino acids are most critical for antibacterial and antibiofilm activity. We have demonstrated that the charged Lys residues can be modified to tune the peptide hydrogel properties (FIGS. 1 and 2).

Mixing of high concentration peptide solutions (0.8-10 mg/ml) (0.08-1% wt/vol) with alkaline buffer lead to rapid (<5 min) hydrogel formation. The hydrogel was antibacterial and showed lower toxicity in vivo than the soluble peptide. PEG-DGL13K also formed hydrogels, which were less toxic than DGL13K-hydrogel.

GL13K contains 4 Lys residues (pKa=10.5). Substituting with Arg residues (pKa=12.5) generates a more soluble peptide, which does not lead to hydrogel formation in the current protocol. Due to the higher pKa of Arg, it is anticipated that more alkaline (=less physiologic) conditions would be required for hydrogel formation of the Arg-substituted peptide (DGL13R).

GL13K hydrogel can be mixed with other hydrogels (e.g., collagen) to modulate the mechanical property. Interpenetrated GL13K fibrils and collagen fiber were observed.

Antimicrobial hydrogels have been described by others. The present invention, however, takes advantage of the unique properties of BPIFA2 GL13 peptides, including reduced toxicity of the PEGylated peptide, anti-biofilm activity, ability to kill drug-resistant bacteria (including bacteria that resist other antimicrobial peptides) and low frequency of bacterial resistance. Also, the mixing with other biomedical and natural polymers makes this IP versatile to modify existing hydrogels, membranes, grafts and scaffolds.

Methods of Use

Methods to produce injectable hydrogels, membranes, grafts and scaffolds containing antimicrobial peptides of the BPIFA2 GL13 peptide family. The materials consist of either solely antimicrobial BPIFA GL13 peptides and counter-ions or interpenetrated fibrils of antimicrobial peptides and other natural or synthetic polymers (e.g., collagen, cellulose, chitosan, elastin, PLA, and/or PLGA).

In one aspect the present invention provides a method for treating a wound in an animal comprising administering the BPIFA2 peptide, composition, hydrogel, nanofibrillar network or tissue scaffold to the animal. In certain embodiments, the wound is a burn wound, a pressure ulcer, a diabetic ulcer, a laceration, a surgical site or a bone fracture. In certain embodiments, the BPIFA2 peptides, compositions and hydrogels can be used as burn wound dressing, surgical site dressing, endodontic (root-canal) treatment, dressing for areas around medical devices or bone/teeth injuries and implants, peri-implantitis, periodontitis and other infections in body tissues or implanted devices.

In certain embodiments, the wound is a bone fracture. In certain embodiments, the treatment involves the administration of a hydrogel, and is performed by injection.

The present invention provides a therapeutic method for preventing or treating a pathological condition or symptom in a mammal, such as a human, wherein an antibiotic activity is implicated and antagonism of its action is desired, comprising administering to a mammal in need of such therapy, an effective amount of BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide.

The present invention also provides a therapeutic method for preventing or treating a pathological condition or symptom in a mammal, such as a human, wherein an anti-inflammatory activity is implicated and antagonism of its action is desired, comprising administering to a mammal in need of such therapy, an effective amount of BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide.

A therapeutic method for preventing or treating a pathological condition or symptom in a mammal, such as a human, wherein sepsis is implicated and antagonism of its action is desired, comprising administering to a mammal in need of such therapy, an effective amount of BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide.

A therapeutic method for preventing or treating a pathological condition or symptom in a mammal, such as a human, wherein peritonitis is implicated and antagonism of its action is desired, comprising administering to a mammal in need of such therapy, an effective amount of BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide.

The present invention also provides a method to treat a microbial infection comprising of administering a therapeutically effective amount of BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide to a mammal. The present invention also provides a method of inducing bacterial agglutination comprising contacting bacteria with a BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide. In certain embodiments, the microbes are gram-negative bacteria. In certain embodiments, the bacteria are *Pseudomonas aeruginosa, Escherichia coli, Klebsiella pneumoniae, Acinetobacter baumanii, Porphyromonas gingivalis* or *Aggregatibacter (Actinobacillus) actinomycetemcomitans*.

In certain embodiments, the microbes are gram-positive bacteria. In certain embodiments, the bacteria are *Staphylococcus aureus, Enterococcus faecalis* or *Streptococcus gordonii*.

In certain embodiments, the microbes are multi-drug resistant gram-negative or gram-positive bacteria of the species listed above.

The present invention provides a compound that includes BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide for use in medical therapy.

In one aspect the present invention provides a BPIFA2 peptide, a hydrogel comprising a BPIFA2 peptide, a nanofibrillar network comprising a BPIFA2 peptide, or a tissue scaffold comprising a BPIFA2 peptide for use in treating a wound.

In one aspect the present invention provides a use of a BPIFA2 peptide, a hydrogel comprising a BPIFA2 peptide, a nanofibrillar network comprising a BPIFA2 peptide, or a tissue scaffold comprising a BPIFA2 peptide to prepare a medicament for prophylactically or therapeutically treating a wound in an animal.

The present invention provides a use of a compound that includes a BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide for the manufacture of a medicament useful for the treatment of a microbial infection in a mammal.

The present invention provides a method of preventing the adhesion of bacteria on a solid substrate comprising contacting the solid substrate with a peptide BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide.

The present invention provides a method of preventing the formation of biofilm of bacteria in vivo by contacting a tissues surface with BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide. In certain embodiments, the tissue is tissue in the gastrointestinal or respiratory system, such as oral or lung tissue, or another mucosal surface.

The present invention provides a method of preventing the formation of a biofilm of bacteria on a solid substrate comprising contacting the solid substrate with BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide. In certain embodiments, the solid substrate is a medical device. In certain embodiments, the medical device is a ventilator tube or a catheter. In certain embodiments, the solid substrate is a polypropylene or PVC surface. In certain embodiments, the solid substrate is titanium or titanium alloys, Co—Cr alloys, Ni—Ti alloys, alumina, zirconia, resin composites, etc.

The present invention provides an expression cassette including a nucleic acid that is less than 150 nucleotides in length encoding a BPIFA2 peptide as described herein. In certain embodiments, the expression cassette further includes a promoter. In certain embodiments, the expression cassette further includes a marker gene. In certain embodiments the marker gene is fused in frame to the BPIFA2 peptide sequence so as to produce a fusion protein containing the BPIFA2 peptide sequence. In certain embodiments the expression cassette further comprises a cleavable sequence that allows the specific release of the BPIFA2 peptide form the fusion protein.

The present invention provides a vector that contains the expression cassette including a nucleic acid that is less than 150 nucleotides in length encoding a BPIFA2 peptide as described herein.

The present invention provides a cell that contains expression cassette including a nucleic acid that is less than 150 nucleotides in length encoding a BPIFA2 peptide as described herein.

The peptide could be administered as a prophylactic during procedures that are known to carry a high risk of infection and biofilm formation. The present biofilm inhibitors are based on a human protein and the initial data support the expectation that they have low toxicity, unlike currently-known biofilm inhibitors (e.g., patulin and PA).

In certain embodiments, the present invention provides a peptide BPIFA2 peptide, a composition comprising a BPIFA2 peptide, a hydrogel comprising a BPIFA2 peptide, a nanofibrillar network comprising a BPIFA2 peptide, or a tissue scaffold comprising a BPIFA2 peptide as described herein that is used in a wound dressing, such as for burn wounds, pressure ulcers, diabetic ulcers, lacerations, surgical sites. In certain embodiments, scaffolds for tissue regeneration are used in surgery, bone fractures, orthopedic implants, implanted medical devices, and other sites that require protection from infection.

In certain embodiments, the membranes described herein are used for guided tissue regeneration, e.g. periodontal surgery or dental implants.

In certain embodiments, the injectable hydrogel described herein can be further mixed with small molecules (e.g. steroid hormones, traditional antibiotics) or biomolecules (e.g. peptides, proteins, carbohydrates) to stimulate tissue regeneration, wound healing or control inflammation and cell attachment (i.e. attract or repel specific cell types).

In certain embodiments, the hydrogel described herein is used as an antibiotic in endodontic (root canal) treatment. In certain embodiments, the hydrogel described herein is incorporated in soft contact lenses as an antiseptic. In certain embodiments, the hydrogel described herein is used as an ink for antibacterial bioprinting.

The terms "treat," "treatment," or "treating" to the extent it relates to a disease or condition includes inhibiting the disease or condition, eliminating the disease or condition, and/or relieving one or more symptoms of the disease or condition. The terms "treat," "treatment," or "treating" also refer to both therapeutic treatment and/or prophylactic treatment or preventative measures, wherein the object is to prevent or slow down (lessen) an undesired physiological change or disorder, such as, for example, the development or spread of an infection. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat," "treatment," or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat," "treatment," or "treating" does not include preventing or prevention.

The phrase "therapeutically effective amount" or "effective amount" includes but is not limited to an amount of a compound that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Method of Making Hydrogels, Membranes, Nanofibrillar Networks and Tissue Scaffolds In certain embodiments, injectable Hydrogels are formed by mixing five (5) volumes of a solution of BPIFA2 peptide (1-10 mg/ml) with one (1) volume of dilute sodium hydroxide (40-100 mM) at room temperature. Hydrogels are formed within 10 min and are stable for at least 24h at room temperature.

Pharmaceutical Compositions

The peptides and compositions of the present invention can be formulated as pharmaceutical compositions and administered to a mammalian host, such as a human patient in a variety of forms adapted to the chosen route of administration, i.e., orally, parenterally, or surgically by intravenous, intramuscular, topical or subcutaneous routes.

Thus, the present peptides and compositions may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as Sodium EDTA; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The peptides and compositions may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid. The present compounds may be applied as a hydrogel comprising a BPIFA2 peptide, a nanofibrillar network comprising a BPIFA2 peptide, or a tissue scaffold comprising a BPIFA2 peptide as described herein.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the peptides and compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the peptides and compositions required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Peptides and compositions of the invention can also be administered in combination with other therapeutic agents, for example, other agents that are useful as antibiotics. Examples of such agents include a protein synthesis inhibitor, a cell wall growth inhibitor, a cell membrane synthesis inhibitor, a nucleic acid synthesis inhibitor, or a competitive enzyme inhibitor. In certain embodiments, the additional agent is an antibiotic such as penicillin, ampicillin, amoxicillin, vancomycin, cycloserine, bacitracin, cephalolsporin, imipenem, colistin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraaminosalicylic acid, or ethambutol.

In certain embodiments, the peptides and compositions of the invention is contacted with a microbe. Accordingly, in one embodiment the invention also provides a composition comprising a compound of the present invention, at least one other therapeutic agent, and a pharmaceutically acceptable diluent or carrier. The invention also provides a kit comprising a compound of the present invention, at least one other therapeutic agent, packaging material, and instructions for administering the compound of the present invention or the pharmaceutically acceptable salt thereof and the other therapeutic agent or agents to an animal to prevent bacterial infection.

In certain embodiments, the peptide of the present invention is produced as a fusion protein of the peptide sequence and a carrier protein. The carrier protein can subsequently be cleaved to release the active peptide. Phage display of active peptides may also be a useful method to present the peptide to cells.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, a-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an a-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

In certain embodiments, the peptides are modified by C-terminal amidation, head to tail cyclic peptides, or containing Cys residues for disulfide cyclization, siderophore modification, or N-terminal acetylation.

As used herein, the term "peptide" describes a sequence of 17 to 50 amino acids or peptidyl residues. Preferably a peptide comprises 7 to 25, or 10 to 21 or 13-17 amino acids. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

By "variant" peptide is intended a peptide derived from the native peptide by deletion (so-called truncation) or addition of one or more amino acids to the N-terminal and/or C-terminal end of the native peptide; deletion or addition of one or more amino acids at one or more sites in the native peptide; or substitution of one or more amino acids at one or more sites in the native peptide. The peptides of the invention may be altered in various ways including amino acid substitutions, deletions, truncations, and insertions. Methods for such manipulations are generally known in the art. For example, amino acid sequence variants of the peptides can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

The invention encompasses isolated or substantially purified peptide or protein compositions. In the context of the present invention, an "isolated" or "purified" polypeptide is a polypeptide that exists apart from its native environment and is therefore not a product of nature. An isolated polypeptide may exist in a purified form or may exist in a non-native environment such as, for example, a transgenic host cell or bacteriophage. For example, an "isolated" or "purified" protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed proteins or partial-length proteins are also encompassed by the present invention. By "fragment" or "portion" is meant a full length or less than full length of the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

The terms "protein," "peptide" and "polypeptide" are used interchangeably herein.

A "variant" of a molecule is a sequence that is substantially similar to the sequence of the native molecule.

As used herein, "sequence identity" or "identity" in the context of two polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated.

The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The polypeptides of the invention encompass naturally occurring proteins as well as variations and modified forms thereof. Such variants will continue to possess the desired activity. The deletions, insertions, and substitutions of the polypeptide sequence encompassed herein are specifically designed to modify the characteristics of the polypeptide, including antimicrobial activity, antimicrobial specificity, peptide stability and solubility and peptide toxicity. When it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 3 amino acids, i.e., 1, 2 or 3) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations." Conservative substitutions may alter some parameters of a peptide (e.g. solubility) without altering other parameters (e.g. antimicrobial activity).

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

The invention will now be illustrated by the following non-limiting Examples.

EXAMPLES

Example 1

Antibacterial Activity of GL13 Peptides

Standard broth dilution assays were performed to determine the Minimal Inhibitory Concentration (MIC) of each peptide against *Pseudomonas aeruginosa* (P.a.) or *Staphylococcus aureus* (S.a.) (Table 2).

TABLE 2

Minimal Inhibitory Concentrations, in vitro toxicity (Hemolysis, LD50) and Therapeutic Index of GL13 peptides.

| Name | P.a. | S.a. | LD50 RBC | Tx Indx |
|---|---|---|---|---|
| LGL13K | 10.4 µg/ml | 20.8 µg/ml | 188 µg/ml | 9-18 X |
| DGL13K | 5.2 µg/ml | 1.3-2.6 µg/ml | 500 µg/ml | 96-384 X |
| DGL13R | 2.6 µg/ml | 1.3-2.6 µg/ml | 500 µg/ml | 192-384 X |
| PEG-LGL13K | 20.8 µg/ml | 83 µg/ml | | |
| PEG-DGL13K | 5-10.4 µg/ml | | | |
| PEG-pro-DGL13K | 10.4 µg/ml | 5.2 µg/ml | 1000 µg/ml | 96-192 X |
| PEG-E4-pro-DGL13K | N.D. | N.D. | N.D. | N.D. |

P.a. = *Pseudomonas* aeruginosa;
S.a. = *Staphylococcus* aureus

The dose causing lysis of 50% (LD50) of human red blood cells (RBC) was determined and the therapeutic index (Tx Indx) was calculated as LD50/MIC.

LGL13K and DGL13K are not soluble in physiological salt solution (PBS). The Arg-substituted peptide DGL13R and PEGylated peptides show increased solubility. In FIG. 1, solubility is measured as the absence of optical density (OD) due to turbidity at 630 nm.

The antimicrobial peptide GL13K can form a hydrogel when the peptide is reacted with dilute sodium hydroxide. Hydrogels were formed by incubating 8.3 mg/ml peptide with 16.7 mM NaOH and incubating at room temperature for 5-10 min. Hydrogels were overlaid with Crystal Violet. Two phases indicate the formation of a hydrogel; Phase mixing indicates the absence of hydrogel. DGL13K, PEG-LGL13K, PEG-pro-DGL13K and LGL13K formed hydrogels. DGL13R and PEG-E4-pro-DGL13K did not form hydrogels (FIG. 2). The antimicrobial peptide polymyxin B does not form hydrogel under these conditions (not shown).

To test antibacterial activity, *S. aureus* (FIG. 3) or *P. aeruginosa* (FIG. 4) were plated on agar and peptide hydrogels placed on top of the bacteria. The plates were incubated to allow a bacterial lawn to grow. LGL13K, DGL13K and PEG-DGL13K hydrogels prevented the growth of *S. aureus*

Figure 3:
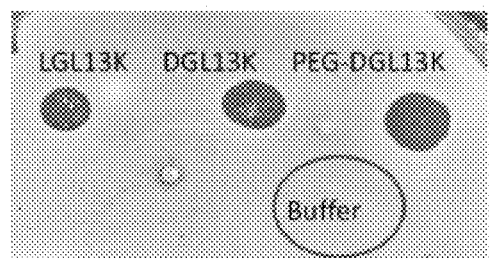
FIG. 3: Peptide hydrogels on *S. aureus*.
Figure 4:
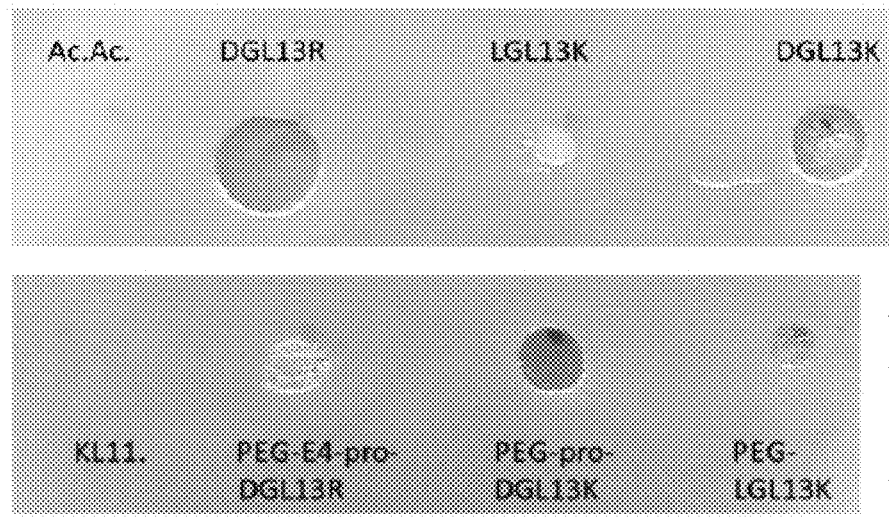
FIG. 4: Peptide hydrogels on *P. aeruginosa* Ac.Ac.=0.01% acetic acid mixed with NaOH (buffer control). KL11 is an inactive control peptide.

(FIG. 3). DGL13R, DGL13K, PEG-proDGL13K effectively prevented the growth of *P. aeruginosa* (FIG. 4). The larger inhibition zone seen for DGL13R is consistent with a lack of hydrogel formation, which allowed the peptide solution to spread on the plate.

The charged residues that allow gelation of the antimicrobial peptides should be Lysines but not Arginines. FIG. 2 above shows that DGL13K but not DGL13R can form hydrogels.

The antimicrobial peptide is comprised of D-amino acids. Both LGL13K and DGL13K kill Gram negative bacteria. DGL13K is more effective against Gram negative bacteria and kills Gram positive bacteria at significantly lower concentrations (Table 2).

Figure 5:
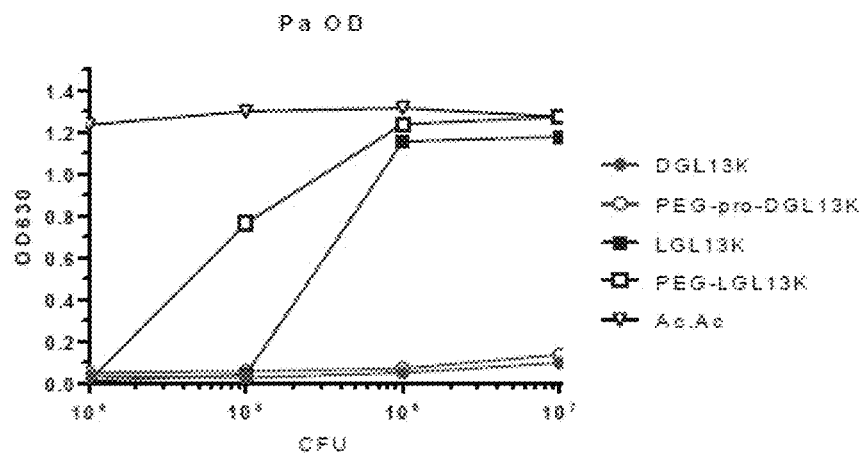
FIG. 5: Hydrogels prevent bacterial growth. Pa=*P. aeruginosa*. Sa=*S. aureus*. Bacteria at the inocula shown were incubated on hydrogels of the listed peptides. Bacterial growth was monitored overnight and expressed as optical density (OD) at 630 nm. Ac.ac.=buffer control.
Figure 5:
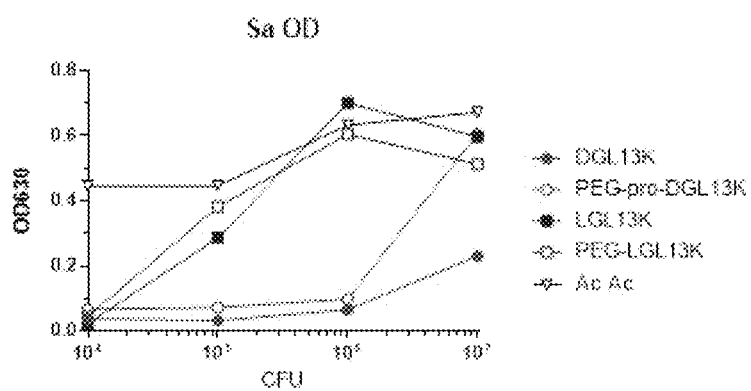

Hydrogels of D-enantiomers are more effectively killing bacteria than hydrogels of L-enantiomers. Hydrogels of D- and LGL13K, and PEGylated version of these peptides were preformed and bacteria were added and incubated overnight (FIG. 5). DGL13K and PEG-pro-DGL13K prevented the growth of bacteria up to a starting load of $10^7$ CFU (Pa) and $10^6$ CFU (Sa). The LGL13K peptides only stopped growth up to $10^5$ CFU (Pa) and $10^4$ CFU (Sa) starting bacterial load. Buffer control did not prevent bacterial growth.

Figure 6:
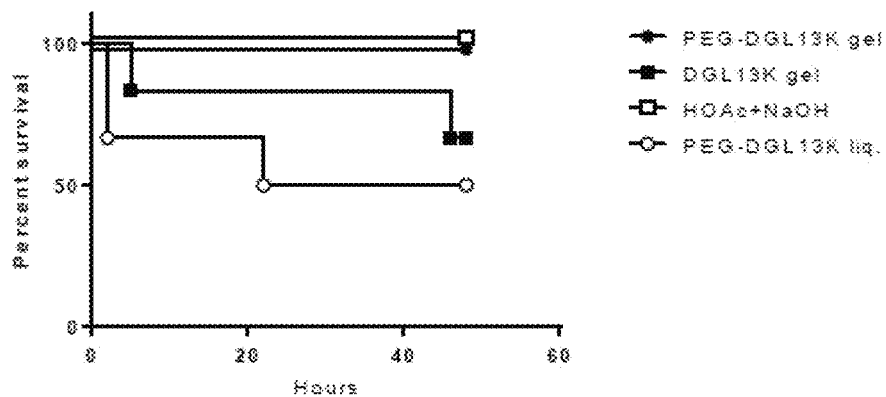
FIG. 6: *Galleria mellonella* (wax moth larvae) were injected with liquid or hydrogel forms of the listed peptide. Larval survival was monitored for 48 h.

The antimicrobial peptide may carry N-terminal polyethyleneglycol unit of MW=116. Antibacterial activity (FIG. 3-5) and hydrogel formation (FIG. 2, 5) are retained in PEGylated peptides with less toxicity in vivo (FIG. 6). PEGylated peptide is more soluble than unmodified peptide (FIG. 1). We have used a PEG of MW=116. It is possible/likely that other sizes would also be effective.

Figure 7:
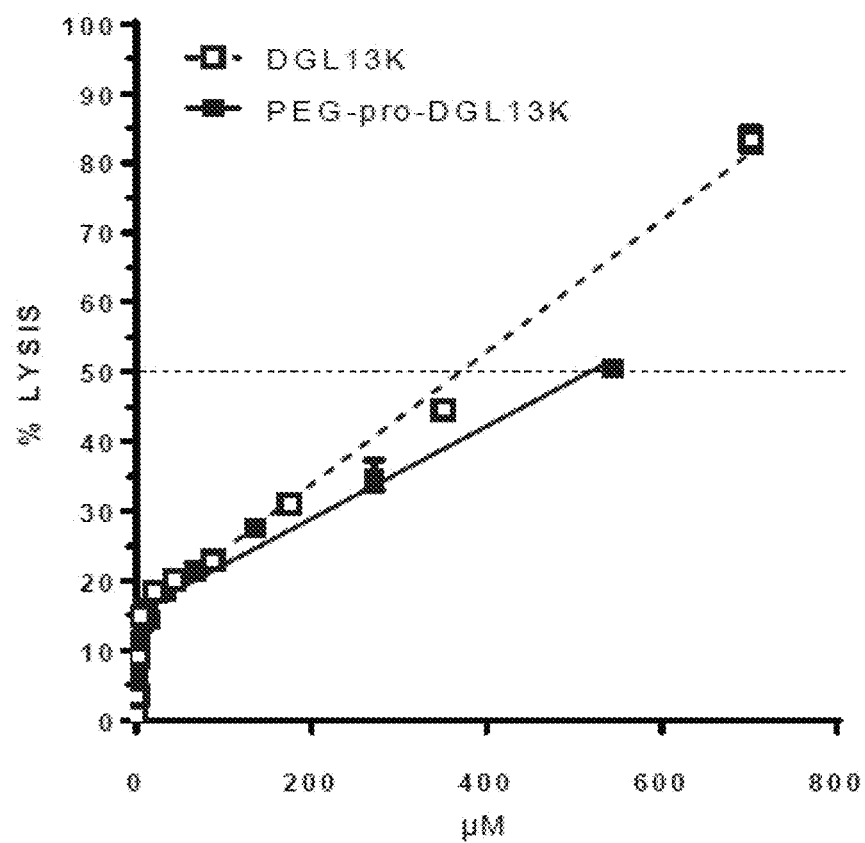
FIG. 7: The in vitro toxicity of soluble DGL13K and PEG-pro-DGL13K was tested against human Red Blood Cells and hemolysis recorded (% lysis compared to dH2O).

The antimicrobial peptide can be extended at the N-terminus by a peptide-linker. A neutral linker peptide retains antibacterial activity (Table 2; FIG. 5) with no increase in toxicity (FIG. 7).

Hydrogels are less toxic in vitro and in vivo than the unmodified peptide. To test toxicity in vivo, hydrogels of DGL13K, PEG-pro-DGL13K (PEG-DGL13K) or liquid PEG-DGL13K were injected into *Galleria mellonella* (waxmoth larvae) and survival monitored for 48 hrs (FIG. 6). The hydrogel of PEG-proDGL13K showed much less toxicity than the soluble form of the peptide. Hydrogel of PEG-pro-DGL13K was less toxic than hydrogel of the unmodified DGL13K peptide.

PEGylated GL13K is less toxic than unmodified peptide. At concentrations above 8 µM, DGL13K shows somewhat higher toxicity than PEG-pro-DGL13K against red blood cells (FIG. 7).

Figure 8:
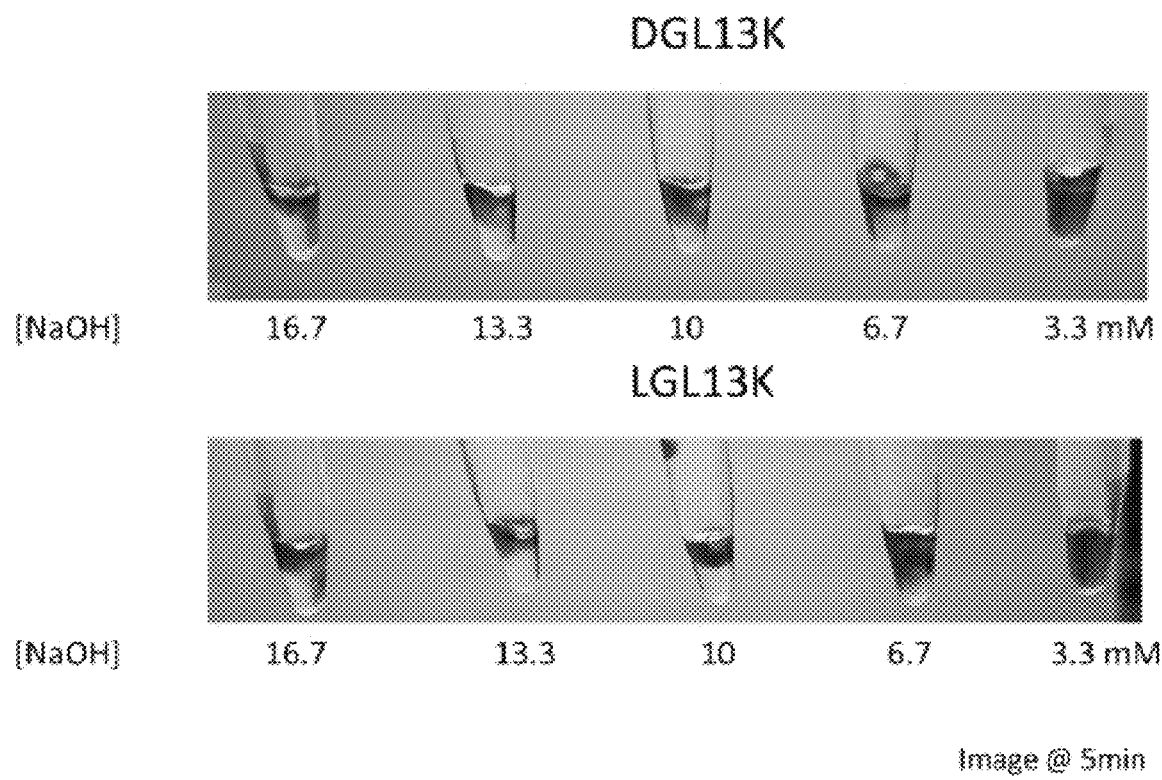
FIG. 8: Hydrogels were formed with 4.2 mg/ml peptide+ sodium hydroxide at the concentrations shown. Hydrogels were overlaid with Crystal Violet. Two phases indicate the formation of a hydrogel; Phase mixing indicates the absence of hydrogel. The hydrogels formed at 6.7 mM NaOH were not stable overnight (not shown).

Hydrogel formation requires a sodium hydroxide concentration of 6.6-16.7 mM. FIG. 8.

Figure 9:
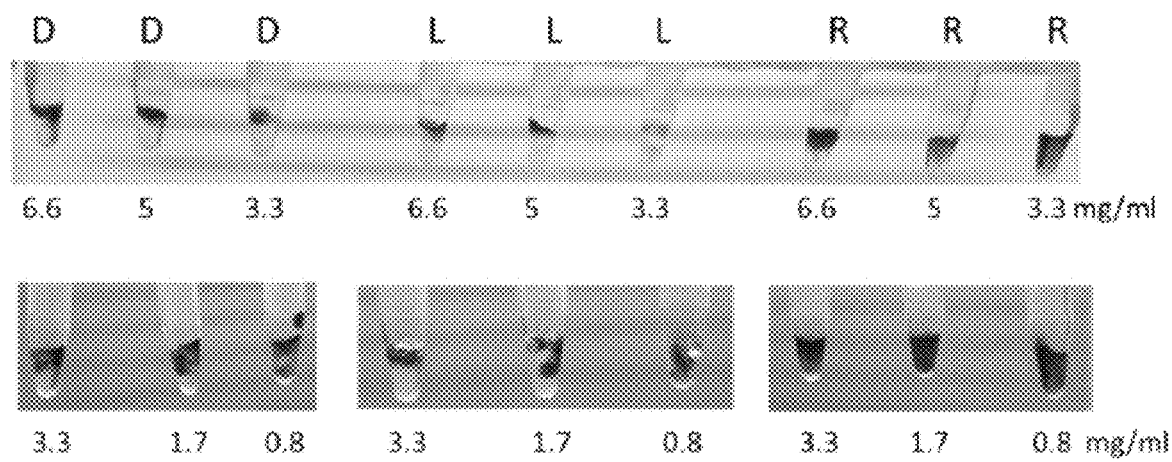
FIG. 9: Hydrogels were formed with 16.7 mM sodium hydroxide and peptides at the concentrations shown. D=DGL13K; L=LGL13K; R=DGL13R. Hydrogels were overlaid with Crystal Violet and imaged within 10 min. Two phases indicate the formation of a hydrogel; Phase mixing indicates the absence of hydrogel.

Hydrogel formation occurs at peptide concentrations above 0.8 mg/ml. FIG. 9.

Example 2

Peptide Treatment Effect Evaluated In Vivo

Studies were performed in a mouse model that resulted in large variations between individual animals, which each received one burn/treatment.

Control: no treatment, vehicle treatment, vehicle+bandage
  DGL13K: peptide in solution, peptide in hydrogel
  SSD: silver sulfadiazine cream (standard of care, positive control)

Figure 10:
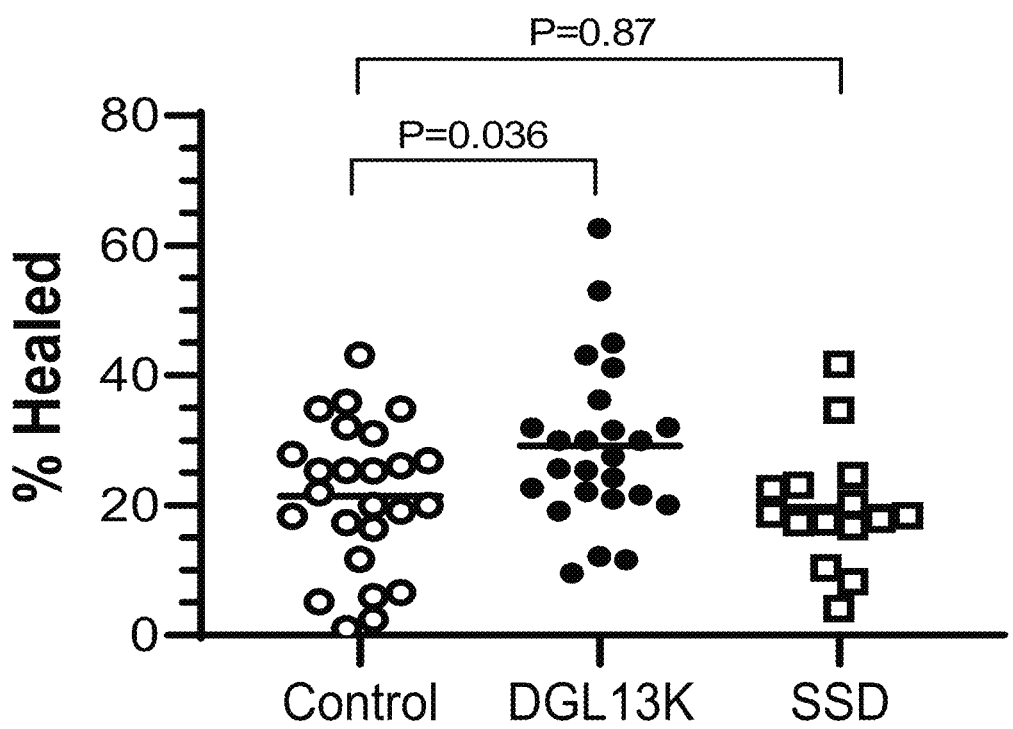
FIG. 10: Healing of mouse skin in combined control (no treatment), DGL13K-treated group and silver sulfadiazine-treated animals. Note: the lack of efficacy of SSD on wound healing has been reported by others (Rosen et al., Silver Sulfadiazine Retards Wound Healing in Mice via Alterations in Cytokine Expression, J. Invest. Derm. 135(5):1459-1462 (2015)).

Seven days after the burn, DGL13K-treated mice showed 36% improved healing compared to the control mice and 48% improved healing compared to SSD-treated mice (FIG. 10).

Example 3

Fabrication and Evaluation of Interpenetrated Membrane Hydrogels

LGL13K can be gelled as a nanofibrillar network. Interpenetrated with a fibrillar network of collagen to form hydrogels or membranes. All data in this Example was collected using collagen, but other natural and synthetic polymers can be used, such as gelatin, silk fibroin, fibrin, elastin, elastin-like polymer, chitosan, starch, alginate, chondroitin sulphate, dextran, agar, carrageenans, gellan gum, cellulose, polycaprolactone, poly(l-lactic acid), poly(lactide-co-glycolide).

Similarly, all the data below were collected using LGL13K, but other peptides with ability to form hydrogels and be antimicrobial (as shown in the results above) can be used to form these gels.

Experiment 1: The interpenetrated LGL13K nanofibrillar network was obtained in a collagen membrane as proof of concept. The schematics of the fabrication process is shown in FIG. 11. The collagen membrane was purchased from ACE Surgical Supply CO., Inc. (Brockton, Mass.) and punched to make disks of 6 mm in diameter. LGL13K was dissolved in deionized (DI) water at a concentration of 14 mg/ml. The collagen disc was submerged in 100 µl LGL13K solution in the well of a 96-well plate at 4° C. overnight. Then 25 µl of 0.1 N NaOH solution was added to the well to gel the LGL13K solution at 4° C. overnight. The LGL13K-incubated collagen disc was washed in DI water for three times and freeze-dried overnight to get the collagen+LGL13K membrane. FIG. 11.

LGL13K forms interpenetrated short nanofibrils and does not alter the original nanostructure of the other hydrogel/membrane.

Experiment 2: the formed collagen+LGL13K membrane was coated with 5 nm Iridium and imaged using a field emission scanning electron microscope (Hitachi SU8230, Tokyo, Japan) at an accelerating voltage of 3 kV.

Result: as shown in FIG. 12, the collagen+LGL13K was composed of large collagen fibers and short GL13K nanofibrils. The collagen fibers were around 200 nm in diameter and presented the typical banding structures of well-assembled collagen. This confirmed that the nanostructure of the collagen fibers was not altered by the interpenetration and interactions with the LGL13K nanofibers. The LGL13K nanofibrils were located either on the surface of the collagen fibers or in the gaps between collagen fibers.

The range of peptide concentration and sodium hydroxide concentration used is the same as for the peptide gel alone. (See Experiment 1 above).

Interpenetrated GL13K peptide nanofibrils with collagen fibrils (collagen+G113K) change the membrane to be much more hydrophobic than the one with only collagen fibers.

Experiment 3: the hydrophobicity of the collagen membrane and the collagen+LGL13K membrane was assessed by water contact angle using the sessile drop method. A droplet of 2 µl DI water was deposited on the top of the membranes.

Figure 13:
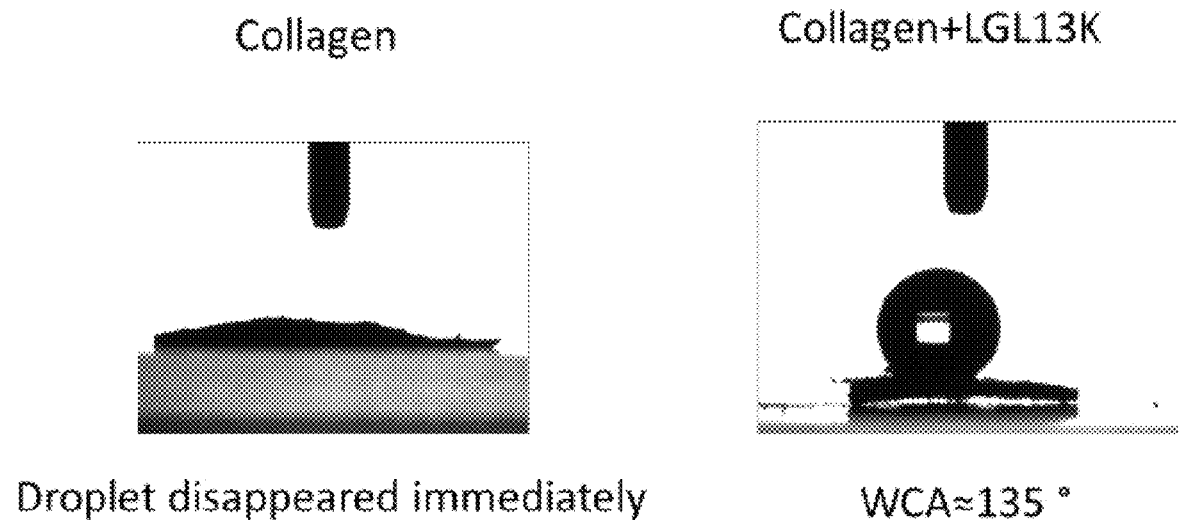
FIG. 13: Water droplet profiles and contact angle (WCA) of collagen and collagen+LGL13K membranes.

Result: the collagen membrane is highly hydrophilic so that the water droplet immediately wets the surface with contact angles close to 0° (most likely this is due to the disappearance of the drop water inside the pores of the hydrophilic collagen membrane). However, the collagen+LGL13K membrane is highly hydrophobic with a stable water contact angle of around 135° C. (FIG. 13).

The high hydrophobicity of collagen+LGL13K membrane reduces its biodegradability from water-borne agents, such as collagenase, compared to collagen membranes.

Experiment 4: the biodegradability of the membrane was evaluated in Type I collagenase solution. The collagenase powder was purchased from ThermoFisher Scientific (Waltham, Mass.) and dissolved in HBSS buffer at the concentrations of 0.05 mg/ml and 0.01 mg/ml. The membrane was placed in the well of a 48-well plate with 1 ml of the collagenase solution. A photo of the remaining membrane was taken after different periods. An analytical balance was used to determine the remaining mass of the sample after different periods of incubation.

Figures 14A, 14B:
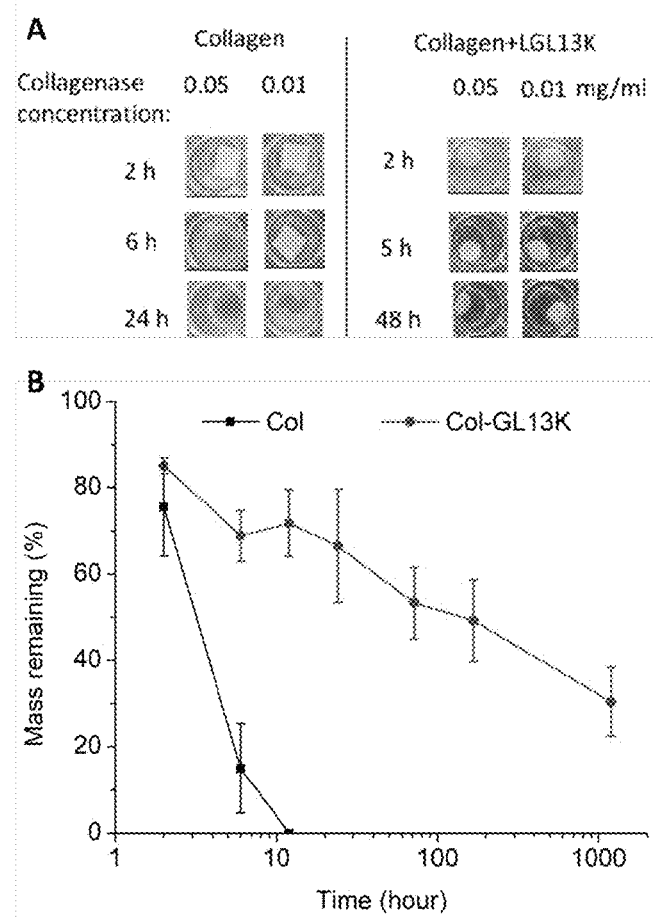
FIGS. 14A and 14B: (a) The biodegradability of the collagen and collagen+LGL13K membranes in 0.05 and 0.01 mg/ml collagenase solutions for up to 48 hours. (b) The biodegradability of the collagen and collagen+LGL123K membranes in 0.01 mg/mL collagenase solutions for up to 10 weeks.

Results: the collagen membranes notably degraded (lost structural integrity) in 0.05 mg/ml collagenase solution within 6 hours and completely degraded (no remaining mass detected) after 10 h in the collagenase solution. Collagen+LGL13K membranes did not notably degrade (less than 50% weight loss) in 0.05 mg/ml collagenase for up to 96 hours (FIG. 14 A and FIG. 14 B).

The interpenetrated collagen+LGL13K membrane has mechanical properties that enable proper handleability.

Experiment 5: rheological properties were measured using a MCR 302 modular compact rheometer (Anton Paar, Graz, Austria) with a set of parallel plates of 8 mm in diameter. A cover was used to prevent water evaporation and to keep temperature constant at 37° C. The samples were wetted in water and placed between plates with a 0.5 mm gap at the measuring position. Excess water was removed using Kimwipes® before each measurement. The measurement was performed using a frequency sweep with two intervals. In the first interval, the sample was equilibrated with a shear strain of 0.5% and an angular frequency of 10 rad/s for 5 min. In the second interval, the shear strain was maintained at 0.5% and the angular frequency was raised from 0.1 rad/s to 100 rad/s in a logarithmic ramp over 30 points. The time interval for each point was set from 10 s to 0.1 s in a logarithmic ramp. The measurements were repeated four times for each group.

Figures 15A, 15B:
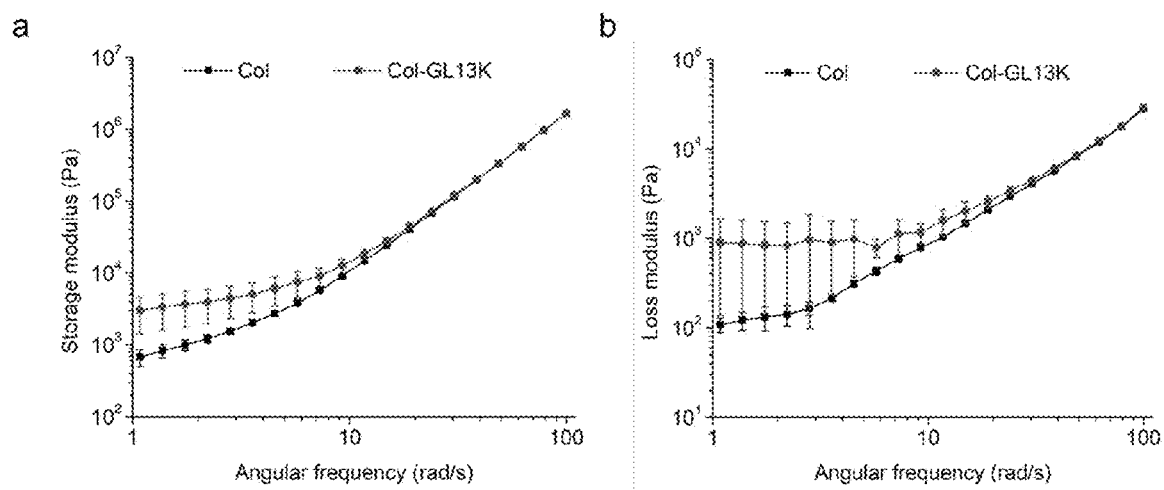
FIGS. 15A-15B: Storage (a) and loss (b) moduli of collagen and collagen+LGL13K as a function of angular frequency.

Results: collagen+LGL13K was stiffer (FIG. 15 A) with also higher loss modulus (FIG. 15 B) than collagen and both in the range of proper handleability.

The collagen+LGL13K membrane is antimicrobial as it reduces the number of live *Streptococcus gordonii* bacteria on the surface of the membrane compared to the collagen membrane.

Experiment 6: The collagen and collagen+LGL13K membranes were incubated with 1 ml of *S. gordonii* culture (starting OD600=0.02) in a 48-well plate for 20 hours in 5% CO2 at 37 ° C. After the incubation, the samples were gently washed by 1×PBS to remove loosely attached bacteria. The viable microbial cells on samples were quantified by Bac-Titer-Glo Microbial Cell Viability Assay (Promega, Madison, Wis.). The luminescence was detected using a multimode microplate reader (BioTek, Winooski, Vt.). The experiments were repeated twice. Bacteria were stained using LIVE/DEAD assay and imaged using a fluorescent confocal laser scanning microscope.

Figures 16A, 16B:
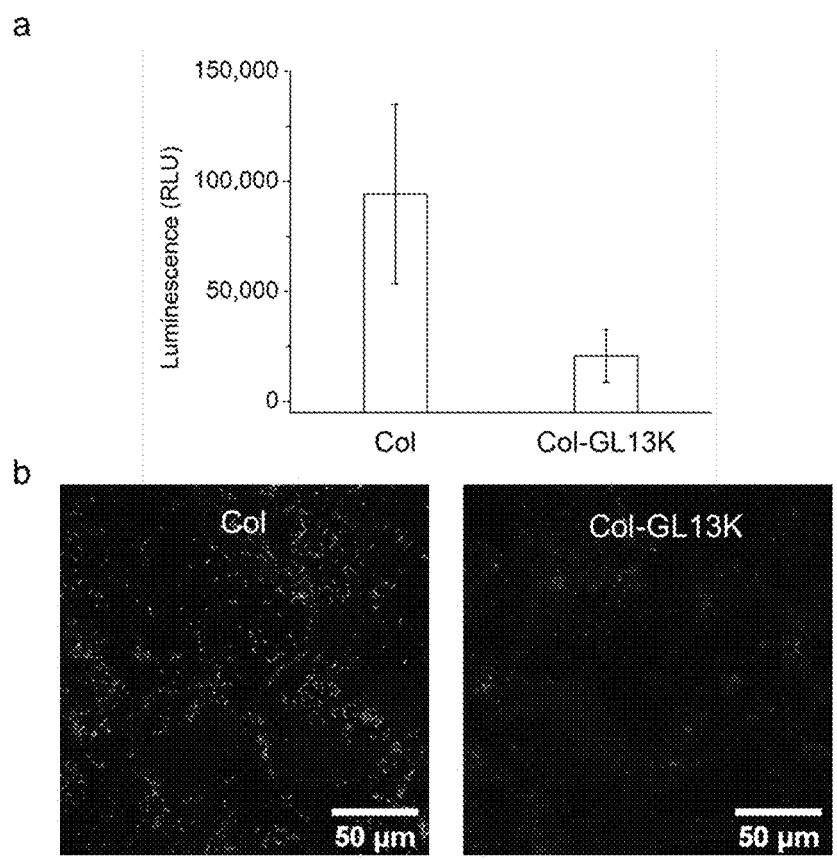
FIGS. 16A-16B: ATP assay (a) and LIVE/DEAD fluorescent image (b) of S. gordonii on collagen and collagen+LGL13K.

Result: The luminescence signal from the ATP of bacteria on the collagen membrane was almost 5 times of that on the collagen+LGL13K membrane (Table 3, FIG. 16 A). It indicated that the collagen+LGL13K membrane significantly reduced the viable bacteria number. Attached bacteria on collagen+LGL13K had compromised cell membrane, indicating the killing activity by contact with the bacteria of collagen+LGL13K (FIG. 16 B).

TABLE 3

Luminescence signal from the ATP of bacteria on the collagen and collagen + LGL13K membranes.

|  | Collagen | Collagen + LGL13K |
|---|---|---|
| Luminescence intensity (RLU) | 94,218 ± 40,779 | 20,725 ± 11,996 |

The interpenetrated collagen+LGL13K membrane is not cytotoxic to human gingival fibroblast.

Experiment 7: The collagen and collagen+LGL13K membrane with a diameter of 6 mm were incubated with human gingival fibroblast for 48 hours. A 6 mm in diameter and 1 mm in thickness glass disc was used as the positive control. The cell metabolic activity was assessed with the MTT assay (PromoCell, Heidelberg, Germany). The optical densities (OD) at 570 nm and 630 nm were read using a multimode microplate reader (BioTek, Winooski, Vt.). After 48 hours, samples were fixed in 4% paraformaldehyde for 30 minutes, permeabilized with 1% Triton X-100, and then blocked in 5% bovine serum albumin (BSA) for 1 hour (all steps at room temperature). Samples were subsequently stained with rhodamine-conjugated phalloidin (R415; Thermo-Fisher) for 20 minutes and then counterstained with 4',6-diamidino-2 phenylindole (DAPI; D9542, Thermo-Fisher) for 10 minutes (all at room temperature). Samples were washed five times in PBS between each step. Visualization was performed on a Leica DM6 B (×20) fluorescent microscope and analyzed in ImageJ (NIH).

Figures 17A, 17B:
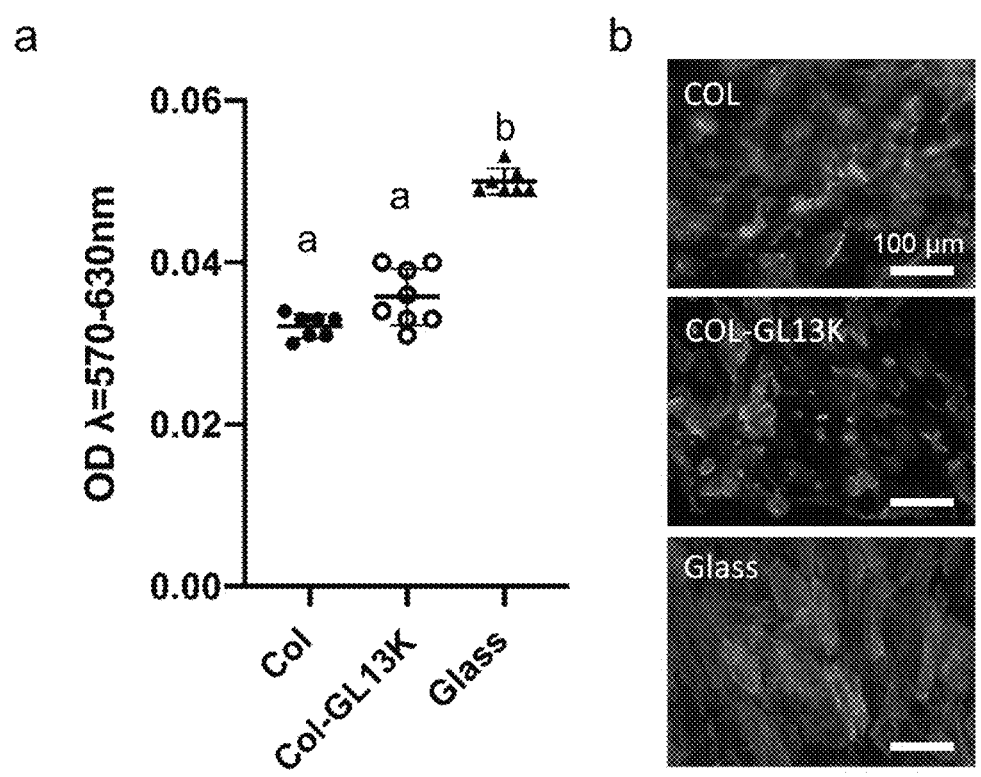
FIGS. 17A-17B: MTT assay (a) and immunofluorescent image (b) of human gingival fibroblasts on collagen, collagen+LGL13K and glass (positive control).

Result: the metabolic activity of human gingival fibroblasts on collagen+LGL13K was similar to that on collagen and comparable to that on the positive control glass discs (FIG. 17 A). Fibroblasts homogeneously colonized collagen+LGL13K and control samples (FIG. 17 B). This demonstrated that the collagen+LGL13K membrane is not cytotoxic to human gingival fibroblasts.

The interpenetrated collagen+LGL13K membrane supports osteoblastic differentiation in vitro.

Experiment 8: Murine pre-osteoblasts (MC3T3-E1; CRL-2593, ATCC) were cultured in Dulbecco's Modified Eagle Medium supplemented with 10% fetal bovine serum and 1% penicillin/streptomycin and used between passages 10-20. Osteogenic differentiation media included an additional 10mM β-glycerophosphate and 50 µg/mL ascorbic acid. Cells were seeded ($1 \times 10^5$) and cultured for 3 days. Then, samples were cultured in osteogenic media for 2 weeks. After this, samples were washed thrice in ice-cold PBS and then lysed in a lysis cocktail (9803S, Cell Signaling Technology) for 15 min on ice. Lysates were cleared with centrifugation (12,000 g, 10 min). ALP activity was then determined based ALP's conversion of colorless p-nitrophenyl phosphate (PNPP; 34047, Thermo Fisher) into a yellow product. ALP activity was normalized to total protein content (Micro BCA Protein Assay Kit, 23235, Thermo-Fisher) per the manufacturer's recommendations. Pre-osteoblast osteocalcin expression (OCN) was quantified with an ELISA (enzyme-linked immunosorbent assay; OST31-K01, Eagle Biosciences) similar to ALP production following the manufacturer's recommendations.

Figures 18A, 18B:
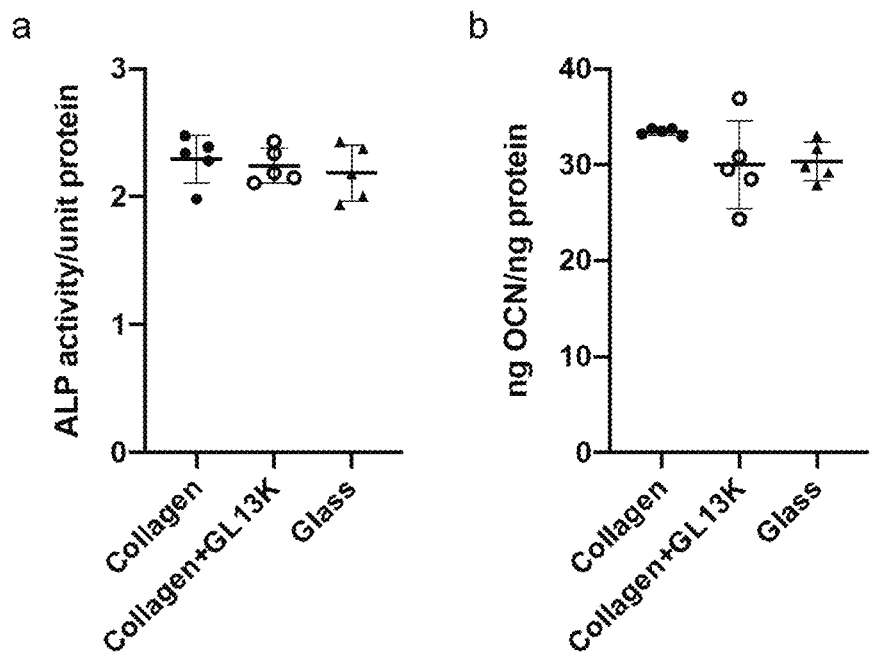
FIGS. 18A-18B: ALP activity (a) and OCN production (b) of murine pre-osteoblasts on collagen, collagen LGL13K and glass (positive control).

Results: Osteogenic activity of pre-osteoblasts on collagen+LGL13K was similar to that on collagen and also comparable to that on the positive control glass discs for both the early osteogenic ALP marker (FIG. 18A) and the late osteogenic osteocalcin marker (FIG. 18B).

The interpenetrated collagen+LGL13K membrane supports bone growth in vivo.

Figures 19A, 19B, 19C:
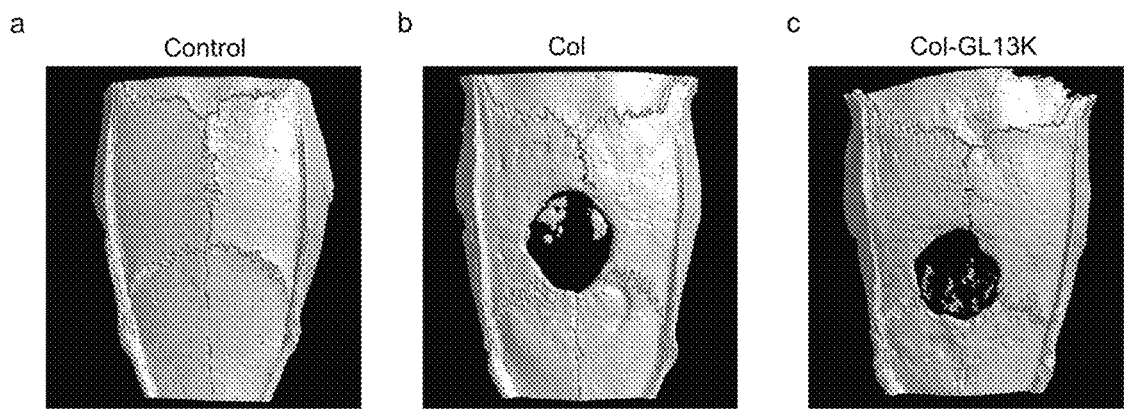
FIG. 19A-19C: Micro-CT images of mice calvarial (a) bone control (no defect) and defects treated with (b) collagen, and (c) collagen+LGL13K groups.

Experiment 9: a rat critical size calvarial defect model was used to evaluate the osteogenic properties of the membranes. A 5 mm calvarial bone defect was created on the cranial apex of 6 w male SD rats. Membranes were placed inside the bone defects and the incision was closed with sutures. After 8 weeks, the rats were sacrificed. The skulls were fixed in 4% paraformaldehyde and imaged by Micro-CT (FIG. 19 A-C).

Results: New bone growth was detected in both the collagen membrane (FIG. 19 B) and collagen+LGL13K membrane (FIG. 19 C), indicating similar osteogenic properties of collagen+LGL13K as collagen.

Although the foregoing specification and example fully disclose and enable certain embodiments, they are not intended to limit the scope, which is defined by the claims appended hereto.

All publications, patents and patent applications are incorporated herein by reference. While in the foregoing specification, certain embodiments have been described, and many details have been set forth for purposes of illustration, it will be apparent to those skilled in the art that additional embodiments and certain details described herein may be varied considerably without departing from basic principles.

The use of the terms "a" and "an" and "the" and similar referents are to be construed to cover both the singular and the plural, unless otherwise indicated herein or clearly contradicted by context.

The terms "comprising," "having," "including," and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the technology and does not pose a limitation on the scope of the technology unless otherwise claimed. No language in the specification should be construed as indicating any non-claimed element as essential to the practice of the technology.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the embodiment.

Embodiments are described herein, including the best mode known to the inventors. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this technology includes all modifications and equivalents of the subject matter recited in the claims appended hereto as permitted by applicable law. Moreover, any combination of the above-described elements in all possible variations thereof is encompassed by embodiments unless otherwise indicated herein or otherwise clearly contradicted by context.

---

What is claimed is:

1. A hydrogel structure material consisting of a BPI Fold Containing Family A Member 2 (BPIFA2) peptide of 13 to 50 amino acids in length comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 10, SEQ ID NO: 11, SEQ ID NO: 12, or SEQ ID NO: 13, wherein the hydrogel structure material is formed by contacting the peptide with an alkaline solution comprising sodium hydroxide, wherein the sodium hydroxide is at a concentration of 6.6 mM to 16.7 mM, and wherein the peptide is at a concentration above 0.8 mg/ml.

2. The hydrogel of claim 1, wherein the peptide is at a concentration of about 0.8 to 10 mg/ml.

3. The hydrogel structure material of claim 1, wherein the BPIFA2 peptide is operably linked to a polyethylene glycol (PEG).

4. The hydrogel structure material of claim 1, wherein the BPIFA2 peptide is operably linked to a therapeutic agent.

5. A composition comprising the hydrogel structure material of claim 1 and a second agent.

6. The composition of claim 5, wherein the second agent is a biomolecule.

7. The composition of claim 6, wherein the biomolecule is selected from the group consisting of a peptide, protein or a carbohydrate.

8. The composition of claim 5, wherein the second agent is a solid support.

9. The composition of claim 8, wherein the solid support is a medical device.

10. A nanofibrillar network comprising the hydrogel structure material of claim 1, and a polymer, wherein the polymer is collagen.

11. A tissue scaffold comprising the nanofibrillar network of claim 10.

12. The hydrogel structure material of claim 1, wherein the BPIFA2 peptide is D- GL13K (SEQ ID NO: 2).

* * * * *

SEQUENCE LISTING

```
<160> NUMBER OF SEQ ID NOS: 14

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Lys Ile Ile Lys Leu Lys Ala Ser Leu Lys Leu Leu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(13)
<223> OTHER INFORMATION: D-amino acid
```

```
<400> SEQUENCE: 2

Gly Lys Ile Ile Lys Leu Lys Ala Ser Leu Lys Leu Leu
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(13)
<223> OTHER INFORMATION: D-amino acid

<400> SEQUENCE: 3

Gly Arg Ile Ile Arg Leu Arg Ala Ser Leu Arg Leu Leu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Lys Ile Ile Lys Leu Lys Ala Ser Leu Lys Leu Leu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(13)
<223> OTHER INFORMATION: D-amino acid

<400> SEQUENCE: 5

Gly Lys Ile Ile Lys Leu Lys Ala Ser Leu Lys Leu Leu
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(17)
<223> OTHER INFORMATION: D-amino acid

<400> SEQUENCE: 6

Leu Gly Gly Ala Gly Lys Ile Ile Lys Leu Lys Ala Ser Leu Lys Leu
```

```
1               5                   10                  15

Leu

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(21)
<223> OTHER INFORMATION: D-amino acid

<400> SEQUENCE: 7

Glu Glu Glu Glu Leu Gly Gly Ala Gly Lys Ile Ile Lys Leu Lys Ala
1               5                   10                  15

Ser Leu Lys Leu Leu
            20

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid

<400> SEQUENCE: 8

Leu Gly Gly Ala
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: D-amino acid

<400> SEQUENCE: 9

Glu Glu Glu Glu
1

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: D-amino acid
<220> FEATURE:
<221> NAME/KEY: MOD_RES
<222> LOCATION: (4)..(4)
<223> OTHER INFORMATION: D-amino acid

<400> SEQUENCE: 10

Leu Gly Gly Ala Gly Lys Ile Ile Lys Leu Lys Ala Ser Leu Lys Leu
1               5                   10                  15

Leu

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(17)
<223> OTHER INFORMATION: D-amino acid

<400> SEQUENCE: 11

Leu Gly Gly Ala Gly Lys Ile Ile Lys Leu Lys Ala Ser Leu Lys Leu
1               5                   10                  15

Leu

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: D-amino acid
<220> FEATURE:
<221> NAME/KEY: MOD_RES
<222> LOCATION: (8)..(8)
<223> OTHER INFORMATION: D-amino acid

<400> SEQUENCE: 12

Glu Glu Glu Glu Leu Gly Gly Ala Gly Lys Ile Ile Lys Leu Lys Ala
1               5                   10                  15

Ser Leu Lys Leu Leu
            20

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: D-amino acid
```

-continued

```
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(21)
<223> OTHER INFORMATION: D-amino acid

<400> SEQUENCE: 13

Glu Glu Glu Glu Leu Gly Gly Ala Gly Lys Ile Ile Lys Leu Lys Ala
1               5                   10                  15

Ser Leu Lys Leu Leu
            20

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Gly Gly Ala
1
```